US008426621B2

(12) United States Patent
Rutherford et al.

(10) Patent No.: US 8,426,621 B2
(45) Date of Patent: Apr. 23, 2013

(54) REFINED EDIBLE OIL HAVING HIGH BENEFICIAL CONSTITUENTS AND METHODS FOR REFINING THEREOF

(75) Inventors: Nahid Rutherford, Stuttgart, AK (US); Don R. McCaskill, Stuggart, AK (US); Gary E. Nelms, Stuggart, AK (US); Larry D. Corley, Stuggart, AK (US)

(73) Assignee: Riceland Foods, Inc., Stuttgart, AR (US)

( * ) Notice: Subject to any disclaimer, the term of this patent is extended or adjusted under 35 U.S.C. 154(b) by 327 days.

(21) Appl. No.: 12/710,001

(22) Filed: Feb. 22, 2010

(65) Prior Publication Data

US 2011/0207953 A1 Aug. 25, 2011

(51) Int. Cl.
*C07C 51/00* (2006.01)

(52) U.S. Cl.
USPC .......... 554/168

(58) Field of Classification Search .......... 554/168
See application file for complete search history.

(56) References Cited

U.S. PATENT DOCUMENTS

| | | | | |
|---|---|---|---|---|
| 5,290,579 | A | 3/1994 | Hitosumatsu | |
| 6,197,357 | B1 * | 3/2001 | Lawton et al. | 426/330.6 |
| 6,506,916 | B2 * | 1/2003 | Bertholet | 554/202 |
| 6,576,298 | B2 * | 6/2003 | Bennett et al. | 427/424 |

OTHER PUBLICATIONS

International Search Report corresponding to PCT/US11/24274 dated Apr. 7, 2011.

Kim, S. K, et al.,"Effect of Caustic Refining, Solvent Refining and Steam Refining on the Deacidification and Color of Rice Bran Oil," 62 JAOCS No. 10, 1492-1495 (1985).

Mattikow, M, "Developments in the Refining of Oils with Sodium Carbonate," 25 JAOCS No. 6, 200-203 (1948).

Takeshita, Y. and Okubo, O. "An Improved Method for the Acid Values of Rice Bran Oil and Its Identification," 14 Transactions of the Kokushikan Univ. Dept. of Engineering, 20-26 (1981).

Krishna, A. G. G., et al. "Acidity of Oryzanol and Its Contribution to Free Fatty Acids Value in Vegetable Oils" 83 JAOCS No. 12, 999-1005 (2006).

American Oil Chemists Society, "AOCS Official Method Ca 5a-40, Free Fatty Acids," (D. Firestone. ed., AOCS Press. 1997).

* cited by examiner

*Primary Examiner* — Deborah D Carr
(74) *Attorney, Agent, or Firm* — SNR Denton US LLP

(57) ABSTRACT

Methods for producing refined rice bran oil that include caustic treatment step(s) in an amount that is less than or equal to a theoretical amount of caustic required to neutralize practically all of the free fatty acids in the rice bran oil, but avoiding addition of excess caustic. An objective is to retain a high level of oryzanol in the refined oil.

14 Claims, No Drawings

REFINED EDIBLE OIL HAVING HIGH BENEFICIAL CONSTITUENTS AND METHODS FOR REFINING THEREOF

FIELD OF THE INVENTION

The present invention generally relates to refined rice bran oil (RRBO) having high gamma oryzanol content and methods of making the same. In particular, the invention relates to RRBO that has 50% or more of the gamma oryzanol retained from crude rice bran oil (CRBO), which is achieved in part by treating the oil with an amount of caustic treatment that is less than or equal to the theoretical amount of caustic required to neutralize all of the free fatty acids in the rice bran oil.

BACKGROUND OF THE INVENTION

Gamma oryzanol (oryzanol) is a natural antioxidant that is a mixture of steryl ferulates, which is found in rice, corn, and barley oils. Oryzanol contributes to the stability of oil in storage and food applications. Specifically, the oryzanol in rice bran oil (RBO) functions as a natural substitute for synthetic antioxidant additives normally used in vegetable oils to enhance or prolong shelf life. Oryzanol, therefore, is a useful substitute for synthetic antioxidant additives such as propyl gallate, butylated hydroxyanisole (BHA), butylated hydroxytoluene (BHT), and tertiary butylated hydroquinone (TBHQ). In addition, evidence suggests that oryzanol may provide numerous health benefits including reducing serum LDL cholesterol.

In crude rice bran oil (CRBO), oryzanol is present in amounts of 1 to 3% of the CRBO; however, conventional caustic refining methods strip away a substantial amount of oryzanol from the final product due to over-treatment of the crude oil with alkali solution(s) during FFA neutralization. Thus, many of the benefits of oryzanol are not retained in RBO refined using conventional alkali treatment.

Crude edible vegetable oil, which includes neutral oil, non-triglyceride materials, such as free fatty acids (FFA), hydratable and non-hydratable phospholipids, moisture, waxes, peroxides and related products, color pigments, and dirt, goes through various processing steps before becoming refined oil product.

During conventional edible vegetable oil processing, a series of steps, often collectively referred to as "refining" are commonly included as part of overall vegetable oil processing. These steps can include one or more of the following: (a) degumming, which is the removal of phosphatides, (b) removal of FFA via neutralization, (c) bleaching, which is the removal of colorant pigments, residual soaps and gums, and pro-oxidant metals, (d) dewaxing, which can occur at different stages throughout the refining process, (e) winterization, which is also known as stearine removal, and (f) deodorization, which is the removal of undesirable volatile impurities, odors, and flavors from the oil. In lieu of degumming, the crude oil can be pretreated based on the non-hydratable phosphatide content of the crude oil with an amount of mineral, organic, or combinations of acids such as phosphoric or citric acids. Typically the amount of mineral or organic acid for the pretreatment step ranges from 300-1000 ppm.

In some cases, depending on plant design or producer's preference, two or more of the above steps may be combined.

In the deodorization step, odorous and volatile impurities as well as residual FFA, small amounts of triglycerides, and other organic impurities will be carried off or stripped out via steam distillation under vacuum as distillate. The temperature and pressure used for the deodorization step will define the amount of distillate produced at this stage.

For the neutralization step, the acidified CRBO can be treated directly with a predetermined caustic dose, or first degummed to remove hydratable and non-hydratable phospholipids from the crude oil and then treated with a caustic dose.

In either case, the conventional caustic treatment applied during the neutralization step includes a caustic dose that contains an amount of caustic that is in excess of the theoretical amount required to neutralize all FFA.

Determination of the excess caustic treatment quantity per conventional alkali refining is based on (a) the concentration of FFA in the crude oil, (b) the amount of acid addition for preconditioning of the crude oil, and (c) the excess caustic over theoretical amount for different types of oils as shown in the formula below. For example, the strength of caustic (NaOH) solution is determined by solution's specific gravity, which is expressed in degrees Baume (Be°).

$$\%\ \text{Caustic Treat} = \frac{(\%\ FFA \times 0.142) + \%\ \text{Excess Caustic} + \text{Amount Pretreatment Acid Addition to Crude}}{\%\ \text{NaOH in Caustic}} \times 100$$

The concentration of the FFA in the crude oil is measured by a standard titration method known to those of ordinary skill in the art The theoretical amount of caustic is calculated from the ratio of the molecular weight (MW) of the caustic material, such as NaOH to the MW of oleic fatty acid.

$$\text{Molecular Weight Factor} = \frac{\text{NaOH Molecular Weight}}{\text{Oleic Fatty Acid Molecular Weight}} = \frac{40}{282} = 0.142$$

The amount of excess caustic used in the conventional methods varies depending on the type of oil and past refining experience with the particular oil(s); however, the total amount of caustic used is always greater than the theoretical amount needed to neutralize the FFA plus the amount of added free acid. These amounts are well known to those of ordinary skill in the art and can be found in standard refining reference books. See Robert R. Allen et al., *Bailey's Industrial Oil and Fat Products*, Fourth Edition, 1982. Daniel Swern ed., John Wiley & Sons.

U.S. Pat. No. 6,197,357 and Mattikow teach production of refined oils rich in at least one unsaponifiable component by refining the CRBO via a weak acid salt. See M. Mattikow, *Development in the Refining of Oils with Sodium Carbonate*, JAOCS 25 (6) pp. 200-203 (1948). These methods reportedly result in the retention of about 75 to 100% of at least one unsaponifiable component in the refined oil. However, U.S. Pat. No. 6,197,357 and Mattikow teach an excess treatment of a weak acid salt in order to effectively neutralize the FFA present in the CRBO.

Japanese Patent Application 10-293157 (JP 10-293157) teaches using a combination of a weak alkali & buffer solution instead of strong alkali solutions to produce, according to JP 10-293157, RRBO with 80% or more of the oryzanol originally present in the CRBO. This application also teaches an excess treatment with weak alkali and buffer solution in order to effectively neutralize the FFA present in the CRBO.

As previously noted, one of the major problems with refining RBO by typical conventional alkali or caustic refining methods is the loss of 93% or more of the oryzanol in the original crude oil. Table 1 below lists the cumulative loss percentage of oryzanol content at various conventional processing steps as discussed in the *Effect of Refining of Crude Rice Bran Oil on the Retention of Oryzanol in the Refined Oil*. A. G. Gopala Krishna, Sakina Khatoona, P. M. Shiela, C. V. Sarmandala, T. N. Indirab, and Arvind Mishrac. *Effect of Refining of Crude Rice Bran Oil on the Retention of Oryzanol in the Refined Oil, JAOCS*, Vol. 78, No. 2 (February 2001).

TABLE 1

| Process | Oryzanol Content after Processing Step (%) | Loss (%) |
|---|---|---|
| Control Rice Bran Oil (Free Fatty Acid, 6.8%) | 1.86 | — |
| Degumming | 1.84 | 1.1 |
| Dewaxing | 1.75 | 5.9 |
| Control Rice Bran Oil + alkali treatment | 0.10 | 94.6 |
| Degummed Rice Bran Oil + alkali treatment | 0.11 | 94.1 |
| Dewaxed Rice Bran Oil + alkali treatment | 0.13 | 93.0 |

As such, there is a need for an economical refining method that results in substantial retention of oryzanol in the refined oil.

SUMMARY OF THE INVENTION

The present invention provides RRBO retaining high levels of naturally occurring oryzanol and methods for producing same. The methods are based on Applicants' discovery of improved systems for accurately determining and neutralizing the FFA content of the crude oil so as to introduce a sufficient amount of caustic to neutralize FFAs, thereby protecting other acidic constituents such as oryzanol and other phenols in the unsaponifiable fraction. Therefore, Applicants have shown that it is possible to process crude oils without excess caustic treatment per conventional refining methods to produce good quality oil with no significant loss of oryzanol.

Additionally, the inventors' discovery of a method of commercially applying accurate measurement of the true FFA content of crude oils rich in phenolic substances, in turn, facilitates maximizing retention of the oil's oryzanol content.

For example, an accurate measurement of FFA can be made by using AB-6B (Fisher Scientific) in place of the longstanding industry standard, PP, as the indicator in titrations to exclude interference by phenolic substances such as oryzanol. When PP is used as the indicator, the total acidity content of the crude oil, which is the summation of FFA, free acid if added to condition the crude, and phenolic compounds is determined. In contrast, AB-6B precludes phenolic compounds present in the oil from the measured acidity. As a result, when AB-6B indicator is used, the measured acidity is the FFA present (and any free acid added) and not the summation of the FFA and the phenolic compounds. Therefore, the inventors have discovered that it is possible to avoid excessive addition of alkali, thus retaining at least 50 to 80% or more, preferably 80%, 85%, 90%, 95%, or more of phenolic substances such as oryzanol of the crude oil regardless of the alkali type and/or strength used to neutralize FFA.

In another aspect of the inventors' method, the actual FFA acidity of the crude oil may be determined by determining the oryzanol percentage (% Oryzanol Content) in crude oil by spectrophotometer or High Performance Liquid Chromatography (HPLC) and determining the total acid value as measured by indicators such as Phenolphthalein, Thymolphthalein, Bromothyolblue, or alpha-naphtyl benzene or the like. In this case, the indicators determine the total acid values; thus caustic addition can be calculated based on the amount of crude's FFA and the amount of free acid added if the crude oil was preconditioned.

Total Acid to be Neutralized=Total Acid Value−(% Oryzanol Content+Added Free Acid for preconditioning of crude oil)

Once the actual FFA value of the crude oil is determined, the alkali dosage for the caustic treatment of the crude oil is calculated based on the actual amount of FFA and the free acid addition if the crude oil was preconditioned, thereby excluding acidity contributed by phenolic compounds such as oryzanol. Since the alkali dosage is based on the actual FFA, the alkali dosage is not "in excess." Additionally, in order to protect oryzanol content from an accidental caustic over-treat, the % oryzanol content of the oil can be monitored during refining and the oil can be intentionally under-neutralized to a pre-determined residual FFA to be left in the oil.

It is therefore an object of this invention to eliminate excess caustic treatment of the crude oil during the refining processes.

It is also an object of certain embodiments of this invention to avoid excessive caustic treatment by improving precision of caustic addition to the oil by use of two-step neutralization that begins with addition of the stronger basic solution and finishes off the neutralization process with a weaker basic solution.

It is an object of the invention to determine a precise neutralization end-point by simultaneously monitoring both oryzanol and FFA contents during refining.

It is an object of this invention to help minimize the refining costs of crude oils such as CRBO while maximizing refining yields and producing refined oils that contain the highest possible levels of beneficial unsaponifiables such as oryzanol.

It is an object of the present invention to produce RRBO that retains a high concentration of oryzanol, specifically, at least 50 to 80% or more, of the oryzanol in the CRBO. For example, the RRBO may contain 50%, 55%, 60%, 65%, 70%, 75%, 76%, 77%, 78%, 79%, 80%, 81%, 82%, 83%, 84%, 85%, 86%, 87%, 88%, 89%, 90% or more of the oryzanol content of the original crude oil.

It is also an object of the invention that the refining method can be practiced with equipment generally available in most edible oil refineries.

In an embodiment of the invention, RRBO having at least 50 to 80% or more of the oryzanol retained from the original crude oil is produced. For example, the RRBO may contain 50%, 55%, 60%, 65%, 70%, 75%, 76%, 77%, 78%, 79%, 80%, 81%, 82%, 83%, 84%, 85%, 86%, 87%, 88%, 89%, 90% or more of the oryzanol content of the original crude oil.

In another embodiment of the invention a neutralization end-point is determined by simultaneously monitoring the content of oryzanol and FFA during neutralization. For example, the amount of FFA is monitored by a standard titration method for colorimetric transition using AB-6B as the indicator, and the content of the oryzanol is monitored by spectrophotometer or High Performance Liquid Chromatography (HPLC).

More specifically, in another embodiment of the invention, crude oil is analyzed for FFA, moisture, and oryzanol contents to establish a baseline. Once the crude oil is treated with calculated caustic dose in the neutralization step, the neutralization reaction that occurs is monitored by analyzing grab samples during the refining stage for FFA and oryzanol contents. These samples are typically taken en route to or right after the centrifuge, but may also be taken at any point afterward. The total acid value or FFA content is determined colorimetrically via titration using various indicators, such as PP, AB-6B or bromothyolblue blue to determine caustic addition. The oryzanol content is determined via spectrophotometer or HPLC. Any decrease in oryzanol concentration of the grab samples from the baseline is indicative of a caustic treatment that is in excess of what is required to neutralize the FFA. As such, a decrease in oryzanol content in a grab sample can be used to signal the end of caustic addition.

In another embodiment of the invention, a method for producing RRBO containing at least 50 to 90% or more of the oryzanol retained from the original CRBO is provided. For example, the RRBO may contain 50%, 55%, 60%, 65%, 70%, 75%, 76%, 77%, 78%, 79%, 80%, 81%, 82%, 83%, 84%, 85%, 86%, 87%, 88%, 89%, 90% or more of the oryzanol content of the original crude oil. This method includes performing a chemical refining step that uses a weak acid salt solution such as sodium phosphate tribasic dodecahydrate (TSP.12$H_2$O, ASTARIS Food Grade Sodium Phosphate Tribasic Dodecahydrate Crystalline, 92%+, UNIVAR USA), other phosphates, sodium carbonates, potassium carbonate, ammonium carbonate, sodium bicarbonate, potassium bicarbonate, ammonium bicarbonate, or other alkalis such as sodium hydroxide, potassium hydroxide and the like to neutralize the CRBO FFA in a single step where the dosing is controlled such that the amount of the TSP treatment is effective to neutralize the FFA to a desirable predetermined set value. This value depends on processing method and can be set as high as 3% or more or as low as 0.05% or less. The optimal neutralization is achieved when residual FFA in the oil is 0.05% or less. For example, the FFA content may be 20%, 15%, 10%, 3.0%, 2.5%, 2.0%, 1.5%, 1.0%, 0.20%, 0.15%, 0.10%, 0.05%, or 0.01% or less.

In another embodiment of the invention, a two-step method for producing RRBO containing at least 50 to 90% or more of the oryzanol retained from the original CRBO is provided. For example, the RRBO may contain 50%, 55%, 60%, 65%, 70%, 75%, 76%, 77%, 78%, 79%, 80%, 81%, 82%, 83%, 84%, 85%, 86%, 87%, 88%, 89%, 90% or more of the oryzanol content of the original crude oil. This method includes performing chemical refining steps that use a combination of a strong alkaline solution such as sodium hydroxide followed by a weak acid salt such as TSP solution. In this embodiment of the invention, two caustic refining steps are applied, first using a strong base, such as sodium hydroxide (NaOH) or potassium hydroxide (KOH), or other bases such as sodium silicate, sodium carbonate, sodium bicarbonate, ammonium bicarbonate, potassium carbonate or the like, to neutralize all but a pre-determined amount of residual FFA in the partially refined crude oil. For example, the oil can be under-treated with significantly less NaOH than is called for by the theoretical amount such that between 0.01 to 5% or more FFA remains behind in the oil. This is followed by treatment with TSP solution to neutralize residual FFA to a value of 3.0% to 0.1% or less. For example, after the TSP treatment, the residual FFA content may be 3.0%, 2.5%, 2.0%, 1.5%, 1.0%, 0.20%, 0.15%, 0.10%, 0.05%, or 0.01% or less. The exact amount of residual FFA that may be left behind after final neutralization may be even higher, depending on whether the oil was degummed before neutralization and the intended application of the refined oil.

In another embodiment of the invention, the method for producing RRBO containing at least 75% or more of the oryzanol retained from the original CRBO uses a neutralizing agent that may be a high concentration of any strong base such as sodium or potassium hydroxide, or other alkali solutions such as sodium silicate, sodium carbonate, sodium bicarbonate, ammonium bicarbonate, potassium carbonate or the like. The oil is treated with an amount of base that is less than the theoretical amount needed to neutralize the FFA such that between 0.01 to 5% or more FFA remains in the partially refined RBO. The amount of the base can be an amount that is effective to neutralize the FFA content such that the residual FFA content in the partially refined RBO may be more than 2.5%, 2.0%, 1.5%, 1.0% 1.4%, 1.3%, 1.2%, 1.1%, 1.0%, 0.9%, 0.8%, 0.7%, 0.6%, 0.5%, 0.4%, 0.3%, 0.2%, or 0.1%.

In another embodiment of the invention, the degumming of the crude oil before refining is excluded from the refining process and at least 50 to 80% of the oryzanol content of crude oil is retained in the refined oil. For example, the RRBO may contain 50%, 55%, 60%, 65%, 70%, 75%, 76%, 77%, 78%, 79%, 80%, 81%, 82%, 83%, 84%, 85%, 86%, 87%, 88%, 89%, 90% or more of the oryzanol content of the original crude oil. The oil is treated with an amount of caustic that is less than the theoretical amount needed to neutralize the FFA such that between 0.01 to 5% or more of FFA remains in the partially refined RBO. The amount of caustic may be an amount that is effective to neutralize the FFA content such that the residual FFA content may be more than 2.5%, 2.0%, 1.5%, 1.0% 1.4%, 1.3%, 1.2%, 1.1%, 1.0%, 0.9%, 0.8%, 0.7%, 0.6%, 0.5%, 0.4%, 0.3%, 0.2%, or 0.1%.

Furthermore, an embodiment of the invention also includes a method for producing oryzanol-rich RRBO having at least 50 to 90% or more of the oryzanol retained from CRBO preconditioned with food grade mineral acids such as phosphoric acid (75% concentration) or organic acids such as citric, acetic, maleic and the like. FFA content of the crude oil is determined via titration using AB-6B as an indicator. For example, the RRBO may contain 50%, 55%, 60%, 65%, 70%, 75%, 76%, 77%, 78%, 79%, 80%, 81%, 82%, 83%, 84%, 85%, 86%, 87%, 88%, 89%, 90% or more of the oryzanol content of the original crude oil. The amount of alkaline material for neutralization is determined based on the total amount of free acid used for CRBO conditioning plus the FFA content of the crude oil minus the intentional and pre-determined amount of residual FFA to be left in the crude oil. The above amount of alkali is added to the crude oil, and neutralization is allowed to occur. After neutralization and determination of residual FFA content using AB-6B in the partially refined crude oil, an amount of weaker solution of the same caustic (or other weaker alkali solutions) is added to neutralize the remaining FFA to a value of 3.0% to 0.1% or less. For example, the FFA content may be reduced to 2.5%, 2.0%, 1.5%, 1.0% 1.4%, 1.3%, 1.2%, 1.1%, 1.0%, 0.9%, 0.8%, 0.7%, 0.6%, 0.5%, 0.4%, 0.3%, 0.2%, or 0.1% or less. After the second neutralization step, conventional refining methods are used to complete the process.

Other systems, methods, features, and advantages of the present invention will be, or will become, apparent to one with skill in the art upon examination of the detailed description. It is intended that all such additional systems, methods, features, and advantages included within this description, be within the scope of the invention, and be protected by the accompanying claims.

DETAILED DESCRIPTION OF THE INVENTION

The present invention solves the problem in conventional edible oil refining techniques that results in refined oil retaining little, if any, unsaponifiables such as oryzanol by discovering various refining techniques that can be used individually or in combination with each other to produce refined oil containing original unsaponifiable content, including those retaining 75% or more of the oryzanol present in the original crude oil. The present invention uses methods, which are further detailed below to produce RRBO having high oryzanol content.

In a first embodiment, a sufficient amount of TSP solution of a sufficient strength for the concentration of FFA in the CRBO is used to neutralize the FFA in the CRBO. TSP addition was based on a 1:1 molar ratio between TSP and FFA. Sufficient TSP dose does not include an excess amount as per conventional methods. TSP is used in place of strong bases such as NaOH, KOH, or carbonates, bicarbonates, sodium silicate, or other alkali solutions which are used in conventional caustic refining.

Preparation of TSP Solution: 100 ml of 23% TSP solution was made by dissolving 25 g of 92% purity TSP crystalline (TSPc) with warm water. The solution was stored at 71° C. (160° F.) to avoid re-crystallization of the solute. Solubility of TSPc in water is temperature dependent during make-up and storage of the solution. Each mole of TSPc contains ¼ mole of NaOH.

Below are examples of experiments conducted illustrating this first embodiment.

Experiment 1

About 431 g of plant Degummed Rice Bran Oil (DRBO) containing 2.92% FFA (determined by AB-6B) and 1.46% oryzanol were neutralized via charging with approximately 70.45 grams of 23% TSP solution (stored at 71° C./160° F.). The oil mixture was mixed on a stirring plate (set at #7 on dial of Fisher magnetic stirrer, cat #14-511-1) for 15 minutes at ambient temperature (22° C./72° F.). Once the FFA content of the oil was reduced to 0.13%, neutralization was ended. The FFA content was measured by using AB-6B as the indicator during titration. The oil mixture was then de-sludged via a centrifuge at 2700 rpm for 5 minutes to separate the refined oil from the soapstock phase. The resulting RRBO had oryzanol content of 1.28%.

Experiment 2

About 431 grams of pre-acidified (1500 ppm food grade 75% concentration $H_3PO_4$, HARCROS Chemicals) CRBO containing 3.86% FFA and 1.6% oryzanol concentration were refined by using approximately 96.49 grams of 23% TSP solution (stored at 160° F.) at ambient temperature 22° C./72° F.). The soft oil was mixed for 15 minutes using a stirring plate (set at #7 on dial of Fisher magnetic stirrer, cat #14-511-1). TSP addition was discontinued once residual FFA was reduced to 0.12%. The content of FFA was determined by titration using AB 6B indicator. The resulting RRBO had oryzanol content of 1.23%.

In a second embodiment, the oil is treated with an amount less than the calculated theoretical amount of caustic solution required to neutralize FFA by utilizing a strong caustic such as sodium or potassium hydroxide or sodium silicate, sodium carbonate, sodium bicarbonate, ammonium bicarbonate, potassium carbonate, etc. to neutralize all but a small predetermined amount of residual FFA in the crude oil. Most of the remaining FFA is then neutralized via a TSP solution.

The treatment amount described above can be set at any pre-determined value; for example, the amount of strong caustic solution can be an amount, depending on the crude quality, that is effective to leave behind approximately 0.01 to 5% or more FFA. For example, the CRBO can be charged with enough strong caustic solution such as sodium or potassium hydroxide, or other alkaline solutions such as sodium silicate, sodium carbonate, sodium bicarbonate, ammonium bicarbonate, potassium carbonate or the like to leave approximately 0.5% or more of the FFA in the crude oil. This partially neutralized oil is then dosed with a sufficient amount of TSP solution until the FFA content of the oil is reduced to below 2.5%, 2.0%, 1.5%, 1.0% 1.4%, 1.3%, 1.2%, 1.1%, 1.0%, 0.9%, 0.8%, 0.7%, 0.6%, 0.5%, 0.4%, 0.3%, 0.2%, or 0.1% or less. After treatment, the RRBO contains 50 to 90% or more of the oryzanol content of the original crude oil. For example, the RRBO may contain 50%, 55%, 60%, 65%, 70%, 75%, 76%, 77%, 78%, 79%, 80%, 81%, 82%, 83%, 84%, 85%, 86%, 87%, 88%, 89%, 90% or more of the oryzanol content of the original crude oil. Two experiments conducted for evaluation of this second embodiment are discussed in the following:

Experiment 3

About 900 grams of pre-acidified (1500 ppm of 75% $H_3PO_4$) CRBO containing 3.79% FFA and 1.69% oryzanol was treated with 24.37 grams of 20% NaOH (from 50% concentration stock NaOH, HARCROS Chemical) until all but 0.75% FFA was neutralized at ambient (22° C./72° F.) room temperature using a stirring plate, (set at #7 dial). The remainder of the FFA was subsequently neutralized with approximately 37.06 grams of 18% TSP solution. The soft oil was mixed for 15 minutes on a stirring plate (set at #7 dial of Fisher magnetic stirrer, cat #14-511-1) until FFA residual reached 0.2% value. The initial FFA content and neutralization endpoint were determined via titration using AB-6B as the indicator. The refined oil contained 1.36% oryzanol.

Experiment 4

An approximately 155,180 pound batch of acidified (1500 ppm of 75% concentration $H_3PO_4$, HARCROS Chemical) CRBO containing 3.9% FFA (determined by using AB-6B as an indicator) and 1.6% oryzanol was refined at the rate of 12,000 pounds per hour with 260.49 pounds per hour of 32° Baume NaOH until the FFA (AB-6B) was reduced to 0.75%. The remaining residual FFA was then neutralized with 629.73 pounds per hour of 18% TSP solution until the FFA value of the oil was reduced to 0.049% (determined by using AB-6B as an indicator). The final oryzanol content of the refined oil was 1.20%.

This experiment confirmed that high retention of the oryzanol in the refined oil can be achieved by neutralizing the majority of FFA by first treating the solution with an amount of NaOH that is less than the theoretical amount of caustic solution required to neutralize FFA, followed by neutralization with TSP to further reduce FFA to a level that can be removed by the deodorizer. This approach provides a significant potential reduction in the cost of chemical reagents while also increasing refining yields, depending on crude oil quality.

In a third embodiment, a 2-Step Caustic process is used to produce RRBO with at least 75% or more of the oryzanol present in the original crude oil. In this method, sodium hydroxide is used as the caustic. The Alternate Refining Method 3 is an economical way to produce RRBO of high quality with low refining loss while retaining 75% or more of the oryzanol present in the crude oil because sodium hydroxide is relatively inexpensive.

The following steps are followed in the 2-Step Caustic (NaOH) Method:

a. determine FFA content of CRBO using AB-6B as an indicator;

b. pre-condition CRBO with mineral or organic acids;

c. calculate initial amount of alkali treatment required to neutralize the amount of added free acid and all but a desired pre-determined amount of FFA content to remain in the partially treated oil and add this amount in the form of higher strength (Baume) caustic (NaOH) solution to the crude oil, mix, and allow sufficient time for neutralization to occur as per conventional refining;

d. determine residual FFA content of the partially neutralized oil using AB-6B as the indicator;

e. calculate the second dose of caustic (NaOH) solution with lower Baume of caustic to further reduce the FFA content to below 2.5%, 2.0%, 1.5%, 1.0% 1.4%, 1.3%, 1.2%, 1.1%, 1.0%, 0.9%, 0.8%, 0.7%, 0.6%, 0.5%, 0.4%, 0.3%, 0.2%, or 0.1% or less.

f. charge the under-treated crude oil with the calculated amount of the lower Baume caustic, allow sufficient time (depending on refinery's caustic addition system set-up) to neutralize the remaining FFA to below 2.5%, 2.0%, 1.5%, 1.0%, 1.4%, 1.3%, 1.2%, 1.1%, 1.0%, 0.9%, 0.8%, 0.7%, 0.6%, 0.5%, 0.4%, 0.3%, 0.2%, or 0.1% or less.

g. complete refining by conventional methods to produce a RRBO that contains 50 to 90% or more of the oryzanol content of the original crude oil. For example, the RRBO may contain 50%, 55%, 60%, 65%, 70%, 75%, 76%, 77%, 78%, 79%, 80%, 81%, 82%, 83%, 84%, 85%, 86%, 87%, 88%, 89%, 90% or more of the oryzanol content of the original crude oil.

Below are pilot plant trials conducted in support of bench trials which illustrate the use of the third embodiment.

Experiment 5

An approximately 160,280 pound batch of pre-acidified (1500 ppm of 75% concentration H3PO$_4$) CRBO containing 2.8% FFA (determined by using AB-6B as an indicator) and 1.62% oryzanol was refined via the 2-Step Caustic (NaOH) Method at the rate of 10,300 pounds of crude oil per hour using 26° and 6° Baume caustic (NaOH) solutions, respectively. Initially, 2.3% FFA content of the CRBO was neutralized with approximately 224.85 pounds per hour of 26° Baume caustic solution, and the remaining FFA was treated with 153.55 pounds per hour of 6° Baume caustic solution until residual FFA content of less than 0.1% (AB-6B) was achieved. The oryzanol content of the refined oil was 1.30%.

Experiment 6

An approximately 152,426 pound batch of pre-acidified (1500 ppm of 75% concentration $H_3PO_4$) CRBO containing 2.8% FFA (as determined by using AB-6B as an indicator) and 1.62% oryzanol was refined via the 2-Step Caustic (NaOH) Method at the rate of 10,300 pounds of crude oil per hour using 26° and 4° Baume caustic (NaOH) solutions, respectively. Initially, 2.3% of the FFA content of the CRBO was neutralized with 224.85 pounds per hour of 26° Baume caustic solution, and the remaining FFA was treated with 195 pounds per hour of 4° Baume caustic solution until FFA (AB-6B) content was approximately 0.1%. The refining endpoint was determined via titration using AB-6B indicator. The oryzanol content of the refined oil was 1.30%.

The above experiments have demonstrated that either strong or weak alkali, independently or in combination of two or more, can be used to neutralize FFA in crude oil without substantial loss of selected desirable unsaponifiable constituents such as oryzanol. Specifically, the methods employ the inventors' unexpected discovery that it is possible to neutralize the FFAs with sodium or potassium hydroxide without destruction of oryzanol since FFA and oryzanol do not react with alkaline reagents simultaneously.

While this development specifically illustrates the retention of oryzanol in RRBO based on eliminating the excess caustic treatment, it should be recognized that minor adjustments in centrifuge operation, bleaching, and deodorization by those experienced in the art may result in superior preservation of oryzanol and other desirable unsaponifiables. While various embodiments of the present invention have been described, it will be apparent to those of skill in the art that many more embodiments and implementations are possible within the scope of this invention. Accordingly, the present invention is not to be restricted except in light of the attached claims and their equivalents.

What is claimed is:

1. A method for producing refined rice bran oil comprising the steps of:

determining the amount of free fatty acids in a rice bran oil;

calculating an amount of a caustic treatment that is less than or equal to a theoretical amount of caustic required to neutralize all of the free fatty acids in the rice bran oil; and neutralizing the free fatty acids with the amount of caustic treatment that is less than or equal to the theoretical amount of caustic required to neutralize all of the free fatty acids in the rice bran oil.

2. The method of claim 1 wherein the caustic treatment is selected from the group consisting of one or more of the chemicals consisting of sodium hydroxide, potassium hydroxide, TSP, sodium silicate, sodium carbonate, sodium bicarbonate, ammonium bicarbonate and potassium carbonate.

3. The method of claim 1 wherein the caustic treatment is selected from sodium hydroxide and TSP solution.

4. The method of claim 1 wherein the caustic treatment is an amount that is effective to neutralize 95.5% or more of the free fatty acid in the rice bran oil.

5. The method of claim 1 wherein neutralizing the free fatty acids comprises the steps of:

conducting a first neutralization step with an amount of caustic treatment that is less than the theoretical amount of caustic required to neutralize all of the free fatty acids in the rice bran oil such that residual free fatty acids remain in the rice bran oil, and conducting a second neutralization step with an amount of caustic treatment that is sufficient to neutralize essentially all of the remaining free fatty acids in the rice bran oil.

6. The method of claim 5, wherein the amount of caustic treatment in the second neutralization step is sufficient to neutralize the remaining free fatty acids to a level that is equivalent to no more than 5% or less of the free fatty acid content of the rice bran oil.

7. The method of claim 5 wherein the amount of caustic treatment in the second neutralization step is sufficient to neutralize the remaining free fatty acids to a level that is from about 0.20 to 0.05% of the free fatty acid content of the rice bran oil.

8. The method of claim 5 wherein the caustic treatment in the second neutralization step uses a weak solution of alkali and the amount of weak solution of alkali is sufficient to neutralize the residual free fatty acids to 0.01% or less.

9. The method of claim 7 wherein the weak solution of alkali is selected from a group consisting of TSPc, tri-sodium phosphate, sodium hydroxide, potassium hydroxide, sodium carbonate, potassium carbonate, ammonium carbonate, sodium bicarbonate, potassium bicarbonate and ammonium bicarbonate.

10. The method of claim 5 wherein the weak solution of alkali is TSPc solution.

11. The method of claim 1 or 5 wherein AB-6B indicator is used to determine the amount of free fatty acids in the rice bran oil.

12. The method of claim 1 or 5 wherein the amount of free fatty acid in the rice bran oil is determined by (1) measuring the oryzanol content of the oil, (2) measuring the total acid content of the oil using phenolphthalien, thymolphthalein, bromothyolblue or alpha-naphtyl benzene and (3) subtracting the oryzanol content from the total acid content to obtain the working free fatty acid content plus added free acid.

13. The method according to claim 1 or 5 further including the steps of:

taking at least one grab sample during the neutralization step;

analyzing the content of the oryzanol in the grab sample via spectrophotometer or High Performance Liquid Chromatography; and analyzing the free fatty acid content of the grab sample via titration method.

14. A refined rice bran oil made according to any of the methods of claims 1-10 further including the step further including a deodorization step.

* * * * *

UNITED STATES PATENT AND TRADEMARK OFFICE

CERTIFICATE OF CORRECTION

PATENT NO. : 8,426,621 B2
APPLICATION NO. : 12/710001
DATED : April 23, 2013
INVENTOR(S) : Nahid Rutherford et al.

It is certified that error appears in the above-identified patent and that said Letters Patent is hereby corrected as shown below:

Title Page, Item (75),

In the Inventors, following Nahid Rutherford, please delete AK, and insert --AR--;
In the Inventors, following Don R. McCaskill, please delete Stuggart, AK, and insert --Stuttgart, AR--;
In the Inventors, following Gary E. Nelms, please delete Stuggart, AK, and insert --Stuttgart, AR--; and
In the Inventors, following Larry D. Corley, please delete Stuggart, AK, and insert --Stuttgart, AR--.

Signed and Sealed this
Thirtieth Day of July, 2013

Teresa Stanek Rea
*Acting Director of the United States Patent and Trademark Office*